United States Patent [19]

Mullarkey

[11] Patent Number: 5,770,401
[45] Date of Patent: Jun. 23, 1998

[54] METHODS AND COMPOSITIONS FOR TREATING ALLERGIC REACTIONS

[76] Inventor: Michael F. Mullarkey, 1422 Eight Ave. West, Seattle, Wash. 98119

[21] Appl. No.: 211,667

[22] PCT Filed: Oct. 14, 1992

[86] PCT No.: PCT/US92/08775

§ 371 Date: Apr. 14, 1994

§ 102(e) Date: Apr. 14, 1994

Related U.S. Application Data

[63] Continuation of Ser. No. 776,624, Oct. 15, 1991, abandoned.

[51] Int. Cl.$^6$ ............................ C12P 21/02; C12N 15/00; C07H 19/00
[52] U.S. Cl. ........................ 435/69.2; 536/27; 536/23.51; 536/24.31; 435/320; 435/235; 435/240; 435/252; 435/255; 330/387; 530/399; 530/351
[58] Field of Search .............................. 435/69, 320, 235, 435/240, 252, 255; 536/27, 23.51, 24.31; 330/387; 530/399

[56] References Cited

U.S. PATENT DOCUMENTS

| | | |
|---|---|---|
| 4,816,436 | 3/1989 | Jacobs . |
| 4,879,374 | 11/1989 | Cerretti et al. . |
| 4,894,333 | 1/1990 | Cerretti et al. . |
| 4,968,607 | 11/1990 | Dower et al. .............................. 435/69 |

FOREIGN PATENT DOCUMENTS

| | | |
|---|---|---|
| 90309875 | of 0000 | European Pat. Off. . |
| 85303701 | 5/1985 | European Pat. Off. . |
| 89311244 | 10/1989 | European Pat. Off. . |
| 3922089 | 12/1990 | Germany . |
| PCT/US88/ 03926 | 11/1988 | WIPO . |
| WO92/10068 | 9/1990 | WIPO . |

OTHER PUBLICATIONS

Chemical Abstracts AN 1991:581211, Jacobs et al., Jan. 1991.
Chemical Abstracts AN 1992:509527, Gillis et al., Jan. 1992.
Leung, et al. *J. Clin. Invest.*, "Expression of Endothelial–Leukocyte Adhesion Molecule–1 in Elicited Late Phase Allergic Reactions" 87:1805–1809 (1991).
Subramanian, et al. *The Journal of Immunology*, "Interleukin 1 Releases Histamine From Human Basophils and Mast Cells In Vitro" 138:271–275 (1987).
Immunex/Receptech—1990 Annual Reports.
Lemanske, Jr., R.F. et al., "Allergy—Principles & Practice" 3rd Edition, Middleton, pp. 224–246 (1988).
Kaliner, M.A., Hospital Practice 22:73 (1987).
Larsen, G.L., Hospital Practice 23:113 (1987).
O'Byrne, P.M. et al., Am Rev Respir Dis 136:740 (1987).
Hargreave, F.E. et al., Eur J Respir Dis 69:16 (1986).
O'Byrne, P.M., Chest 90:575 (1986).
Dolovich, J. et al., J. Allergy Clin. Immunol. 83:521 (1989).
Barnes, P.J., The New England Journal of Medicine 321:1517 (1989).
Toogood, J.H., J. Allergy Clin. Immunol. 83:528 (1987).
Mullarkey, M.F., New Eng. J. Med. 318:603 (1988).
Tracey, N.J., Nature 330:662 (1987).
Fanslow, W.C. et al., Science 248:739 (1990).
Jacobs, C.A., et al., The Journal of Immunology 146:2983 (1991).
Dolovich, J. et al., J. Allergy Clin. Immunol. 49:43 (1972).
Solley, G.O. et al., The Journal of Clinical Investigation 58:408 (1976).
Atkins, P.C. et al., J. Allergy Clin. Immunol. 75:239 (1985).
Barnes, P.J., The American Journal of Medicine 85:64 (1988).
Bascom, R. et al., J. Allergy Clin. Immunol. 81:580 (1988).
Bascom, R. et al., Am Rev Respir Dis 138:406 (1988).
Beasley, R. et al., Am Rev Respir Dis 139:806 (1989).
Bochner, B.S. et al., J. Allergy Clin. Immunol. 86:830 (1990).
Bonini, S. et al., J. Allergy Clin. Immunol. 86:869 (1990).
Boulet, L–P et al., J. Allergy Clin. Immunol. 71:399 (1983).
Boushey, H.A. et al., Am Rev Respir Dis 131:312 (1985).
Bousquet, J. et al., The New England Journal of Medicine 323:1033 (1990).
Cartier, A. et al., J. Allergy Clin. Immunol. 70:170 (1982).
Chung, KF, Thorax 41:657 (1986).
Cockcroft, D.W. et al., J. Allergy Clin. Immunol. 79:734 (1987).
Cockcroft, D.W. et al., Clinical Allergy 7:503 (1977).
De Monchy, Jan G.R. et al., Am Rev Respir Dis 131:373 (1985).
Dolovich, J. et al., J. Allergy Clin. Immunol. 52:38 (1973).
Dvoracek, J.E. et al., J. Allergy Clin. Immunol. 73:363 (1984).
Frew, A.J. et al., J. Allergy Clin. Immunol. 85:533 (1990).
Friedlaender, M.H., Annals of Allergy 67:5 (1991).
Gleich, G.J., J. Allergy Clin. Immunol. 70:160 (1982).
Gronneberg, R. et al., Allergy 36:201 (1981).
Gronneberg, R. et al., Clinical Allergy 15:167 (1985).
Howell, C.J. et al., Am Rev Respir Dis 140:1340 (1989).
Iliopoulos, O. et al., Am Rev Respir Dis 138:400 (1988).
Kaliner, M., J. Allergy Clin. Immunol. 73:311 (1984).
Kelley, J., Am Rev Respir Dis 141:765 (1990).
Lemanske, Jr., R.F. et al., J. Clin. Invest. 83:1 (1989).
Leung, D.Y.M. et al., J. Clin. Invest. 87:1805 (1991).
Lichtenstein, L.M., Hospital Practice, pp. 119–142 (1988).
Marini, M. et al., Am. J. Respir. Cell Mol. Biol. 4:519 (1991).
Massey, W.A. et al., The Journal of Immunology 143:1875 (1989).
Mattoli, S. et al., J. Allergy Clin. Immunol. 87:794 (1991).

(List continued on next page.)

*Primary Examiner*—Keith MacMillan
*Attorney, Agent, or Firm*—James C. Weseman, Esq.

[57] ABSTRACT

Methods and compositions for treating allergic reactions, including cutaneous, ocular, nasal and Bronchial allergic disease, are disclosed. Interleukin-1 and Tumor Necrosis Factor receptors, and analogues thereof, are employed which bind the respective effector competitively and thereby suppress allergic reactions.

10 Claims, 1 Drawing Sheet

OTHER PUBLICATIONS

Mullarkey, M.F., J. Allergy Clin. Immunol. 88:272 (1991).
Naclerio, R.M. et al., The New England Journal of Medicine 313:65 (1985).
Nadel, J.A., J. Allergy Clin. Immunol. 73:651 (1984).
Pienkowski, M.M. et al., J. Allergy Clin. Immunol. 76:729 (1985).
Pipkorn, U. et al., The New England Journal of Medicine 316:1506 (1987).
Poothullil, J. et al., J. Allergy Clin. Immunol. 57:164 (1976).
Sampson, H.A., Hospital Practice, pp. 111–128 (1987).
Sullivan, T.J., "Is Asthma Curable? An Inflammatory Perspective", Internal Medicine Grand Rounds, pp. 1–46 (Jun. 1, 1989).
Umemoto, L. et al., J. Allergy Clin. Immunol. 58:60 (1976).
Waring, N.P., The Journal of Medical Consultation, pp. 1–8 ((Reprint) Oct. 1988).
Wilson, M.C. et al., The Journal of Respiratory Diseases (Aug. 1986).
Kips, J., et al. "Tumor Necrosis Factor Causes Bronchial Hyperresponsiveness in Rates", American Review Of Respiatory Disease, 1992, vol. 145, pp. 332–336.
Ohkawara, Y., el al., "Human Lung Mast Cells and Pulmonary Macrophages Produce Tumor Necrosis Factor–$\alpha$ in Sensitized Lung Tissue After IgE Receptor Triggering", American Journal Of Respiratory Cell And Molecular Biology, 1992, vol. 7, pp. 385–392.

Broide, D., et al., "Cytokines in Symptomatic Asthma Airways", Journal Of Allergy And Clinical Immunology, 1992, vol. 89, pp. 958–967.

Kay, et al., "Messenger RNA Expression of the Cytokine Gene Cluster, Interleukin 3 (IL–3), IL–4, IL–5, and Granulocyte/Macrophage Colony–stimulating Factor, in Allergen–induced Late–phase Cutaneous Rections in Atopic Subjects", Journal Of Expeimental Medicine, 1992, vol. 173, pp. 775–778.

Sim, T.C., et al., "Detection of Inflammatory Cytokines in Nasal Secretions (NS) of Allergic Subjects Following Antigen Challenge", Journal Of Allergy And Clinical Immunology, 1992, p. 216.

Fick, R., et al., "Bronchoalveolar Lavage in Allergic Asthmatics", American View Of Respiratory Diseases, 1987, vol. 135, pp. 1204–1209.

Bernstein, I.L., "Bronchoalveolar Lavage and Asthma: Sampling the Humors Speeds Up", Journal Of Allergy And Clinical Immunology, 1987, vol. 79, pp. 320–323.

Spector, S., "Bronchodilators and Bronchial Provocation", Provocative Challenge Procedures: Background And Methodology, 1989, Futura Publishing Company, Mount Kisco, N.Y., pp. 451–517.

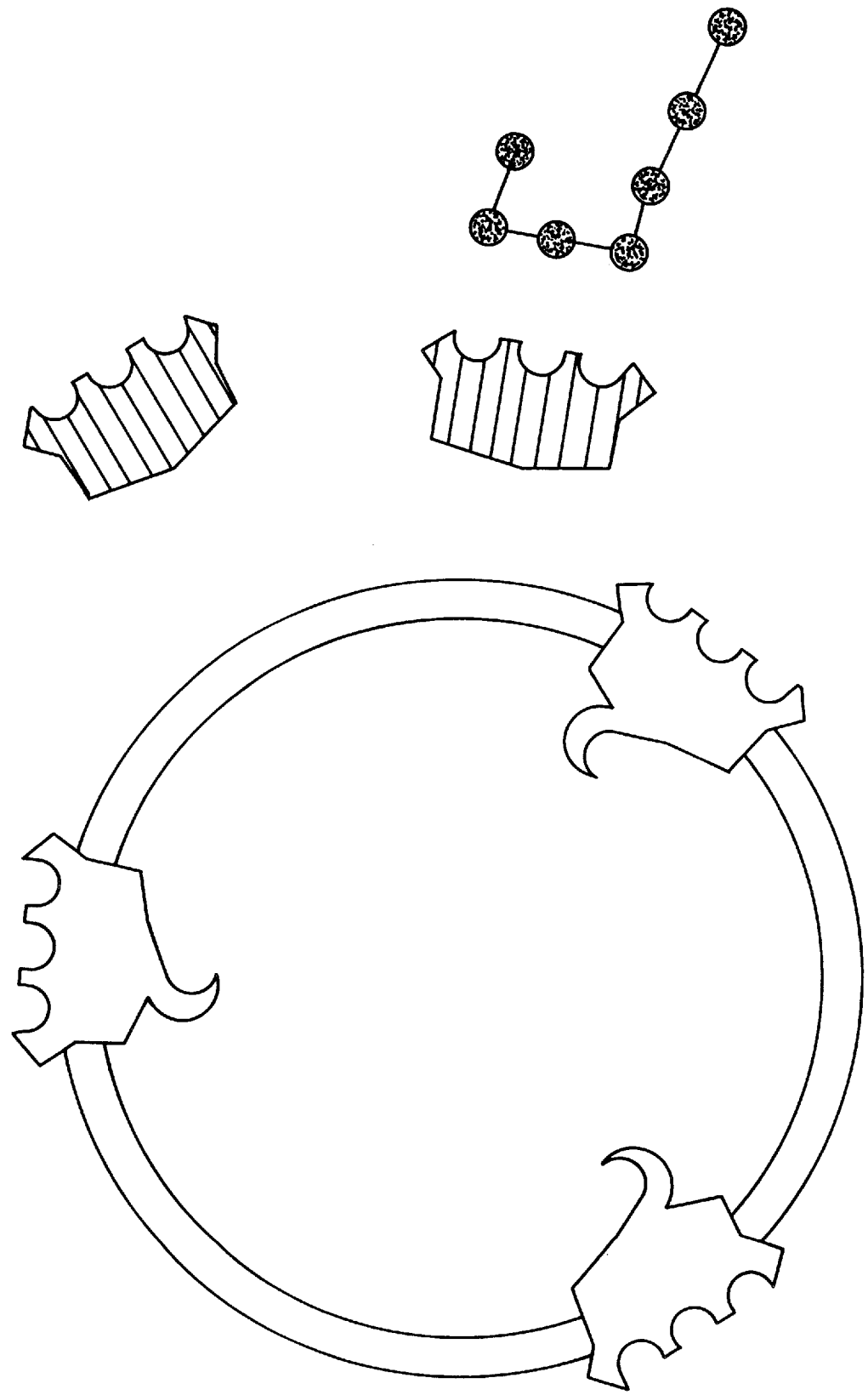

METHODS AND COMPOSITIONS FOR TREATING ALLERGIC REACTIONS

RELATED APPLICATION DATA

This application is a 371 of PCT/US92/08775, filed Oct. 14, 1992, which is a continuation of U.S. patent application Ser. No. 07/776,624, filed Oct. 15, 1991 and now abandoned.

TECHNICAL FIELD

The present invention relates to methods and compositions for treating allergic reactions, and, more particularly, for treating bronchial asthma, rhinitis, rhinoconjunctivitis, conjunctivitis, and dermatitis.

BACKGROUND OF THE INVENTION

An allergic reaction is any abnormal or altered reaction to an antigen (or "allergen"). Typically such a reaction is characterized by hypersensitivity of the body to specific substances, whether protein, lipid or carbohydrate in nature. Allergic reactions may be local, e.g. contact dermatitis, or systemic, e.g. anaphylaxis.

Among allergic diseases, bronchial asthma is one of the most significant. In most urban hospitals, it is the leading cause of admission of children. Current medical practice accepts asthma in afflicted individuals to be an unavoidable, incurable illness. While suppression of symptoms is achieved to a degree sufficient to avoid death, urgent medical visits, disturbed sleep, and days lost from work are typically unavoidable.

The disease is generally associated with dyspnea, wheezing, and cough, as well as reversible airway obstruction and airway hyperreactivity to nonspecific stimuli. These responses have been observed in two phases, early and late (Lemanske, Jr., R. F. and M. A. Kaliner, In: *Allergy, Principles & Practice* (3rd Ed.) pp. 224–246 (1988). See also Kaliner, M. A., *Hosp. Prac.* 22:73 (1987); Larsen, G., *Hosp. Prac.* 23:113 (1987)).

Inhalation of allergens by sensitized subjects typically results in an early phase response characterized by bronchoconstriction within 10 minutes of inhalation, reaching a maximum within 1 to 2 hours. In some subjects, the airway narrowing recurs after 3 to 4 hours (i.e. a late phase response), reaching a maximum during the next few hours (O'Byrne, P. M. et al., *Am. Rev. Respir. Dis.* 136:740 (1987)). This late phase reaction is thought to be due to the cellular phase of inflammation (Hargreave, F. E. et al., *Eur. J. Respir. Dis.* 69(Suppl 147):16 (1986); O'Byrne, P. M., *Chest* 90:575 (1986); Dolovich, J. et al., *J. Allergy Clin. Immunol.* 83(Suppl):521 (1987)).

No complete, long-lasting remissions of asthma have been described in response to any existing therapeutic strategies. For example, systemically administered glucocorticosteroids are potent antiasthmatics; however, the symptoms of the disease are only temporarily suppressed and this is at the cost of well-known side effects, including osteoporosis, weight gain, hypertension, and diabetes (Barnes, P. J., *New Eng. J. Med.* 321:1517 (1989)). Inhaled steroid therapy also has complications (See Toogood, J. H., *J. Allergy Clin. Immunol.* 83(Suppl):528 (1987)). Low-dose methotrexate has been offered as a substitute to steroids, particularly for patients for whom the side-effects of steroids are the most devastating (Mullarkey, M. F., *New Eng. J. Med.* 318:603 (1988)). However, methotrexate, while frequently substituting for toxic doses of corticosteroids, has significant inherent toxicity. Furthermore, it does not eliminate the need for periodic corticosteroids.

There is a great need for new approaches to treatment of allergic disease. Specifically, there is a need for therapy that produces long-lasting anti-inflammatory effect without harm to the patient.

DISCLOSURE OF THE INVENTION

The present invention relates to methods and compositions for treating allergic reactions, including cutaneous, ocular, nasal, gastrointestinal and bronchial allergic disease.

In accordance with the present invention, at least one member selected from the group consisting of Interleukin-1 (IL-1) receptors, Tumor Necrosis Factor (TNF) receptors, and receptor analogues thereof which bind the respective effector, is selectively employed to treat allergic reactions. The present treatment is expected to have many of the beneficial effects of corticosteroids—however, without the toxicity associated with these agents.

One aspect of the present invention contemplates using soluble IL-1 receptors to treat inflammation in tissues. In certain embodiments, this method comprises contacting inflamed tissue with a therapeutic preparation comprising soluble IL-1 receptors. In other embodiments, the inflamed tissue is skin and the inflammation is contact dermatitis, urticaria, angioedema or atopic dermatitis. In additional embodiments, the ocular tissue is inflamed and the inflammation is allergic conjunctivitis. In still other embodiments, the nasal tissue is inflamed and the inflammation is rhinitis. In yet additional embodiments, the lung tissue is inflamed and the inflammation is bronchial asthma.

The present invention also contemplates using such receptors or receptor analogues in combination with other pharmaceuticals (e.g. corticosteroids) to treat inflammation in tissues. In certain embodiments, this method comprises contacting inflamed tissue with a therapeutic preparation comprising a mixture of such receptors and pharmaceuticals such as corticosteroids (e.g. prednisone) and antihistamines.

In other embodiments, the present method comprises contacting inflamed tissue with a therapeutic preparation comprising, in combination, both TNF and IL-1 receptors.

The present invention also contemplates using an allergic assay to screen for anti-allergic drugs. In one embodiment, the present invention comprises using a skin test to measure anti-inflammatory characteristics of pharmaceuticals.

Therapeutic compositions containing such receptors and analogues thereof are also provided in accordance with the present invention.

BRIEF DESCRIPTION OF THE DRAWING

The single FIGURE schematically depicts exogenous receptors (shaded) competitively binding effectors (linked beads) to inhibit the binding of the effectors to endogenous receptors in a cell membrane.

DETAILED DESCRIPTION OF THE INVENTION

The present invention relates to methods and compositions for treating allergic reactions, and particularly, without limitation, bronchial asthma, rhinoconjunctivitis, conjunctivitis, dermatitis, urticaria, chronic bronchitis, allergic and non-allergic rhinitis and inflammatory lung disease. In accordance with the present invention, a therapeutic composition comprising at least one member selected from the group consisting of Interleukin-1 (IL-1) receptors, Tumor Necrosis Factor (TNF) receptors, and receptor analogues thereof which bind the respective effector, is applied exogenously to inflamed tissues. The present invention contemplates the use of IL-1 receptors, TNF receptors, analogues thereof which bind the respective effector or combinations and mixtures thereof, in a therapeutic preparation.

It is presently considered desirable that the receptors and their analogues will be soluble in a medium appropriate to the particular application contemplated. As used herein, the term "soluble" shall mean sufficient solubility in the selected medium so that the receptors are capable of migrating to a position wherein they are able to bind with the endogenous effector, unless a contrary meaning is clear form the context in which the term is used.

As used herein, the term "effector" shall mean IL-1 and/or TNF interchangeably, unless a contrary meaning is clear form the context in which the term is used.

As used herein, the term "substantial" shall mean an amount sufficient to cause a detectable therapeutic effect, unless a contrary meaning is clear form the context in which the term is used.

IL-1 and IL-1 Receptors

Interleukin-1α (IL-1α) and Interleukin-1β (IL-1β) are distantly related polypeptide hormones which play a central role in the regulation of immune and inflammatory responses (See Cerretti et al., U.S. Pat. Nos. 4,894,333 and 4,879,374, each hereby incorporated by reference). These two proteins were originally both classified as IL-1, based on a shared lymphocyte activation factor activity and a common major cellular source, i.e. activated macrophages. As information has accumulated from studies using purified natural and recombinant IL-1 molecules, it has become clear that IL-1α and IL-1β each mediate most, if not all, of the wide range of activities previously ascribed to IL-1. The basis for this nearly identical spectrum of biological activities is thought to be that a single class of plasma membrane IL-1 receptors bind both IL-1α and IL-1β.

The existence of IL-1 plasma membrane receptors is now well-established. While original structural characterizations of the IL-1 receptor were limited to estimates of the molecular weight of this protein by gel filtration, by SDS-PAGE analysis of covalent complexes formed by chemical cross-linking between the receptor and $^{125}$I-IL-1 molecules, and by immunoprecipitation of labeled surface proteins, one of the receptors has now been cloned and expressed in high yield (See Dower, U.S. Pat. No. 4,968,607 assigned to Immunex Corporation, hereby incorporated by reference).

TNF and TNF Receptors

Tumor Necrosis Factor (TNF-α) plays a critical role in the development of acute pulmonary failure and injury. When released into the lung, TNF-α has devastating effects, causing rapid and diffuse tissue injury. This is presumably a direct result of its known effects on endothelial cells and granulocytes, as well as its induction of other mediators such as IL-1, prostaglandins, and platelet-activating factor. When TNF-α is induced in the lungs of animals by the inhalation of endotoxin, airways develop a pattern of reactivity that is characteristic of bronchial asthma (See Pauwels, R. A. et al., Am. Rev. Resp. Dis. 141:540 (March 1990)).

The use of blocking antibodies has made it possible to ablate the toxic action of TNF-α. Baboons can be protected from a lethal intravenous doses of E. coli organisms by prior administration of monoclonal anti-TNF-α(ab') fragments (See Tracey, N. J., Nature 330:662 (1987)).

Tumor Necrosis Factor-α and TNF-β receptors have been isolated and DNA sequences encoding these secretory proteins have been described (See Smith et al., European Patent Application No. 90309875.4 (Publication No. 0418014A1), assigned to Immunex Corporation, hereby incorporated by reference; See also U.S. patent application Ser. Nos. 07/405,370, 07/421,417, and 07/523,635, hereby incorporated by reference).

Receptor Analogues

The present invention also contemplates the use of receptor analogues, and in particular IL-1 receptor analogues and TNF receptor analogues, as therapeutic agents. IL-1 receptor analogues are those compounds which act in an analogous manner to competitively bind IL-1 and inhibit the binding of IL-1 to endogenous IL-1 receptors. An example of such an analogue is described in European Patent Application No. 343684, hereby incorporated by reference. In that case, the analogue is a polypeptide inhibitor of Interleukin-1. See also U.S. patent application Ser. Nos. 07/199,915, 07/238,171, 07/248,521, and 07/266,531, each hereby incorporated by reference.

Such analogues which fall within the scope of the invention also include truncated molecules, and molecules with amino acid additions, substitutions and deletions, wherein regions of the receptor molecule not required for effector binding have been altered or deleted.

The analogues of the present invention share as a common, feature the ability to competitively bind the respective effector to a degree sufficient to display a therapeutic effect when used in the practice of the present invention.

The Use of IL-1 Receptors and TNF Receptors

Since the IL-1 proteins are primary regulators of immunological responses, some investigation has been made into the ability of IL-1 receptors to modify immune responses. For example, Fanslow, W. C. et al., Science 248:739 (1990) describes the regulation of alloreactivity in vivo by a soluble form of the IL-1 receptor. They found that systemic administration of the receptor prolonged the survival of heart allografts. In addition, Jacobs, C. A. et al., J. Immunol. 146:2983 (1991) describes the use of soluble IL-1 receptor to suppress experimental autoimmune encephalomyelitis. These researchers found that interperitoneal administration of the receptor reduced the severity of the disease.

In contrast to these previous uses of IL-1 receptor, the present invention contemplates the topical use of IL-1 receptor on inflamed tissue. In particular, the present invention contemplates the topical, as well as the parenteral use of IL-1 receptor to suppress the early and late phase response in allergic reactions, including the late phase response in bronchial asthma.

Similarly, the present invention contemplates the topical use of TNF receptor on inflamed tissue. In particular, the present invention contemplates the topical, as well as the parenteral use of soluble TNF receptor to suppress the early and late phase response in allergic reactions, including the late phase response in bronchial asthma.

While the benefits conveyed by treatment according to the present invention are not dependent on a precise understanding of the mechanism(s) by which the subject receptors achieve a therapeutic result, it is believed that the suppression of allergic responses is accomplished by competitive binding of the exogenously supplied, receptors and/or analogues thereof to the respective effector, thereby inhibiting the binding of the effector to endogenous receptors on the tissue, as schematically portrayed in the Figure.

In the manner thus illustrated, IL-1 receptors or TNF receptors supplied exogenously are expected to competitively bind to IL-1 or TNF, respectively, thereby inhibiting the binding of the effector to the endogenous receptor.

In practicing the method of the present invention, the therapeutic preparation will be administered to a host in need of anti-allergic treatment at a therapeutically effective dosage level. The lowest effective dosage levels can be determined routinely by initiating treatment at higher dosage levels and reducing the dosage level until relief from allergic reaction is no longer obtained. Generally, therapeutic dosage levels will range from about 0.01–100 µg/kg of host body weight.

Therapeutic Preparations and Combinations

The present invention contemplates using therapeutic compositions of the present receptors or analogues thereof to treat inflammation in tissues, as well as therapeutic preparations comprising, in combination, both TNF and IL-1 receptors. Furthermore, the present invention also contemplates using IL-1 receptors, TNF receptors, receptor analogues, and combinations thereof in combination with corticosteroids or other antiinflamatory drugs or molecules in a therapeutic preparation to treat inflammation in tissues.

Where combinations are contemplated, it is not intended that the present invention be limited by the particular nature of the combination. The present invention contemplates combinations as simple mixtures as well as chemical hybrids. One example of the latter is where the receptor is covalently linked to a pharmaceutical such as a corticosteroid, or where two receptor types are joined. For example, covalent binding of the distinct chemical moieties can be accomplished by any one of many commercially available cross-linking compounds. Further examples of such chemical hybrids include combinations of the receptors together or with other biologically active or inert molecules prepared to utilize the effects of IL-1 receptor and/or TNF receptor. Such hybrid or fusion molecules can be constructed using the techniques of genetic engineering. Similar such molecules have been created by several methods utilizing promoter genes (See, e.g., Feng, G. et al., *Science* 241:1501 (1988)).

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as sprays (e.g. intranasal aerosols) for topical use. However, they may also be prepared either as liquid solutions or suspensions, or in solid forms including respirable and nonrespirable dry powders. Oral formulations (e.g. for gastrointestinal inflammation) usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The receptors of the present invention are often mixed with diluents or excipients which are physiologically tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

The following examples serve to illustrate certain preferred embodiments and aspects of the present invention and are not to be construed as limiting the scope thereof.

EXPERIMENTAL

In the experimental disclosure which follows, the following abbreviations apply: eq (equivalents); M (Molar); µM (micromolar); N (Normal); mol (moles); mmol (millimoles); µmol (micromoles); nmol (nanomoles); kg (kilograms); gm (grams); mg (milligrams); µg (micrograms); L (liters); ml (milliliters); µl (microliters); cm (centimeters); mm (millimeters); µm (micrometers); nm (nanometers); and °C. (degrees Centigrade).

Example 1

This example describes the use of soluble IL-1 receptor to reduce the cutaneous allergic reactions following the intradermal administration of antigen.

Early and late phase responses have been observed following bronchial challenge with such antigens as ragweed pollen and house dust. Importantly, these responses in lung tissue correspond in time to the early and late phase reactions in skin following intradermal challenge with similar antigens (See Dolovich, J. and D. C. Little, *J. Allergy Clin. Immunol.* 49:43 (1972); See also Solley, G. O.. et al.,*J. Clin. Invest.* 58:408 (1976)). Skin reactivity to allergen, especially the Late Phase Reaction (LPR) skin test is believed to be predictive of events occurring in the lungs of asthmatics.

The LPR skin test is performed by intradermally injecting subjects on the forearm with test solution. The test solution contains the challenging antigen. Controls receive test solution without challenging antigen. The injection site is thereafter examined at intervals up to 96 hours. The diameters of the reactions are measured in two perpendicular directions and the characteristics are noted at different times.

Most subjects exhibit a dual reaction, the LPR beginning at the 4 hour point and reaching a peak at the 8–12 hour point. The LPR gradually subsides over a 24 hour period. At the peak, the injection site is characterized by erythema, warmth, edema, pruritus and/or tenderness. The LPR is more extensive in area and produces greater discomfort then the early phase reaction.

In this example, the LPR skin test is performed on individuals; all have previously had a dual response (early and late) to intradermal challenge with antigen as described above. Dust mite antigen is used (*D. pteronyssinus;* Allergy Laboratories of Ohio; 30,000 AU/ml). The soluble IL-1 receptor (Immunex Corp.; Seattle, Wash.) stock concentration is 10 mg/ml. Eight test solutions are prepared for intradermal injections (0.1 ml each) using TB syringes and disposable needles. Four intradermal test sites are used on each forearm.

Two test solutions are controls. Histamine phosphate (Allermed Labs; 1.8 mg/ml) is used as a positive control, and saline is used as a negative control. The six remaining test solutions all contain dust mite antigen; three contain IL-1 receptor (final concentration 1.65 mg/ml) while the other three contain saline. Three concentrations of the antigen are evaluated (final concentrations: 1:500,000, 1:200,000, and 1:100,000).

The area of the wheal reaction is marked on the skin with a ball-point pen. Clear adhesive tape is then applied to the marked skin. The tape with the pen markings is removed from the skin and taped on paper with 0.1 mm squares. The wheal reactions are then calculated by counting the squares within the pen-marked area.

At twenty minutes post injection, the control allergen injection (i.e. containing no receptor) at the lowest concentration produces a wheal more than half the area of the histamine reaction after subtracting the response to the diluent control. By contrast, the wheal produced by injections containing IL-1 receptor are At two hours the early phase subsides. The LPR peaks between eight and 13 hours. At its peak, the control allergen injection (i.e. containing no receptor) at the lowest concentration produces a wheal larger than that observed at 20 minutes, while the wheal produced by injections containing IL-1 receptor are reduced by at least 50 percent.

The results of this example, while specific for IL-1 receptors, nonetheless shows the general applicability of using an allergic assay to screen for anti-allergic drugs. Indeed, this skin test is appropriate to measure anti-inflammatory characteristics of any pharmaceutical.

If desired, a pathologic assessment can be made of the allergic reaction in addition to measuring the wheal visually in the simple skin test. At eight hours a punch biopsy can be taken at one or more of the allergen sites on each forearm. Standard hematoxylin and eosin staining can be performed on formalin-fixed, paraffin-embedded sections. The assessment is made according to the pattern and type of cellular infiltration at the biopsy sites. The sites can be graded on a 0 to 3 scale (none, mild, moderate or severe on the basis of presence and extent of i) perivasfular infiltrate, ii) interstitial infiltrate and edema, and iii) leukocytoclasis. Particular note can be taken with regard to the presence of lymphocytes, eosinophils, macrophages, granulocytes and any other cellular element which is increased in number or unique to normal skin.

Example 2

This example describes the use of soluble IL-1 receptor to reduce the LPR following conjunctival provocation with antigen.

Ocular involvement is common in allergic conditions. It can be the result of systemic allergic symptoms or, indeed, the main focus of allergic disease.

With respect to specific ocular allergies, allergic rhinoconjunctivitis, atopic keratoconjunctivitis, vernal conjunctivitis, giant papillary conjunctivitis, and contact allergy have been identified as the primary types. The most commonly seen form of ocular allergy is the red itchy eyes that accompany allergic rhinitis during the allergy season.

Usually ocular symptoms are overshadowed by nasal or respiratory symptoms. However, in some cases the ocular symptoms predominate. Patients typically complain of red, swollen, itchy eyes, and scant mucous discharge. Itching is an important symptom for ocular allergy since most patients with allergy have itching, and very few other ocular conditions are associated with itching. Other common ocular reactions include giant papillary conjunctivitis (associated with contact lenses) and contact allergy (caused frequently by soaps, shampoos, and eye makeup).

To study ocular involvement, allergists have developed protocols to measure conjunctival allergic response. Conjunctival provocation tests in allergic individuals have been used to confirm the diagnosis of allergy, study the physiologic changes accompanying the allergic reaction, sample the cells and mediators of the allergic response, and evaluate anti-inflammatory therapy.

The conjunctival provocation test (CPT) is a good way of determining the presence or absence of allergy. This is particularly true when a skin test is negative or equivocal. Moreover, the CPT has been found to be safe; the cornea is not affected, and patient discomfort is mild and transient.

Eosinophilia is normally absent in conjunctival scrapings taken from nonallergic individuals. The presence of conjunctival eosinophilia is considered to be a diagnostic indicator of allergic conjunctivitis, and the severity of the disease appears to correlate with the level of major basic protein in tears.

The tear fluid can also be sampled to evaluate the mediators of ocular inflammation. Tear IgE levels have been measured in allergic patients and in general, there is a correlation between the tear and serum IgE levels. This correlation exists when serum IgE is greater than 100 IU/ml and tear IgE is greater than 4 IU/ml.

To evaluate the severity of the response, the eye can be examined with a strong flashlight, or if available, a slit-lamp microscope. The allergic conjunctive appears inflamed and edematous. Rather than intense redness and prominence of blood vessels, the conjunctiva has a pinkish or milky appearance.

In the present example, inhibition of the ocular symptoms in the LPR is examined; the presence of inflammatory cells in the tear film is correlated with the occurrence of ocular symptoms in the LPR time period.

Ten ryegrass-sensitive patients with hay fever conjunctivitis and ten nonallergic subjects without ocular disease are challenged by weekly topical administration of ryegrass allergen for 4 weeks with 10 μl of four different allergen doses (10,000, 32,000, 100,000, and 320,000 BU/ml of ryegrass allergen) (Pharmalgen, Pharmacia Diagnostics AB, Uppsala, Sweden). Albumin diluent (Pharmacia), is used to dilute the allergen. Five of the patients and five of the nonallergic subjects are given allergen premixed with IL-1 receptor. The other five patients and subjects are given allergen without IL-1 receptor. Importantly, the allergic patients and control subjects have no clinical symptoms before ocular provocation.

The CPT involves introducing allergen to the lower conjunctival fornix of one eye by applying 10 μl of different dilutions of ryegrass in albumin prepared at the time of testing. The concentration used were 10,000, 32,000, 100,000, and 320,000 BU/ml. The other eye was used as a control; at the same time the control eye received 10 µl of albumin.

The challenge solution is administered to the contralateral eye in both patients and control subjects. Clinical conjunctival evaluation with tear-fluid cytology is assessed in both eyes before administration of allergen or buffer 20 minutes, one hour, and six hours after challenge. In both the allergic patients and control subjects, the following ocular symptoms, both subjective and objective, are evaluated by a physician: hyperemia, edema, tearing, and itching. Each symptom is scored from 0 to 4+ and graded as follows: 0—absent; 1+—mild; 2+—moderate; 3+—severe; and 4+—very severe. The sum of all scores (maximal clinical score, 16) obtained from each item represented the intensity of the clinical reaction at each time point.

A microcapillary tube (Sigma Chemical Co., St. Louis, Mo.) is used to collect 2 µl of tears from the inner canthus without touching the ocular surface. Such collection of tears is a noninvasive technique which allows repeated sampling without conjunctival trauma. Tears are spread on a glass slide, air-dried, and stained with Wright-Gemsa (Diff-Quick, Baxter Healthcare Corp., Gibbstown, N.J.). All identifiable cells on each slide are counted at original magnification ×1000 using light microscopy. Five types of cells are scored: epithelial cells, neutrophils, eosinophils, lymphocytes, and monocytes. All participants are first examined prior to provocation to assure that there is no significant difference in the baseline levels of inflammatory cells in the tear fluid of allergic patients compared with levels of the control subjects.

Following provocation, all allergic subjects receiving allergen without IL-1 receptor exhibit evidence of an immediate hypersensitivity ocular reaction with all allergen doses; allergic subjects receiving allergen together with IL-1 receptor, exhibit a significantly reduced response. The conjunctival response in allergen-challenged (no receptor) eyes of the allergic patients is also statistically significant compared with the albumin diluent-treated eyes. A significant number of neutrophils are detected in eyes challenged with 320,000 BU/ml of ryegrass allergen (no receptor) compared with the those receiving this dose together with IL-1 receptor.

The highest allergen dose causes the recruitment of a significant number of eosinophils and lymphocytes to the tear fluid 6 hours after provocation (i.e. in late phase) in those eyes challenged with allergen without receptor. This increase in eosinophils in the tear fluid is not seen in allergic patients receiving allergen with receptor.

Example 3

This example describes the use of soluble IL-1 receptor to reduce the LPR in nasal tissue following inhalation of antigen.

Patients with allergic rhinitis often have immediate symptoms after antigen challenge (the early phase response), followed several hours later by a recurrence of symptoms (the late-phase response). This example involves a controlled study of asymptomatic subjects in the pollen-free winter months.

Sixteen patients with seasonal allergic rhinitis due to grass or ragweed pollens are selected. All subjects have a positive intradermal skin test to 10 PNU (protein nitrogen units) or less of antigen extract, and all have previously had a dual response (early and late) to nasal challenge with antigen.

Ragweed and mixed-grass pollen extracts (timothy, orchard, June and meadow grass in a ratio of 3:2:3:2) are purchased from Greer Laboratories (Lenoir, N.C.); lactated Ringer's solution and oxymetazoline hydrochloride (Afrin, Schering, Kenilworth, N.J.) are purchased from the hospital pharmacy.

At the time of the challenge, oxymetazoline hydrochloride is sprayed into the nose (two sprays per nostril) of all patients to prevent mucosal congestion, which would interfere with the collection of nasal secretions. It has been shown previously that this dose of oxymetazoline does not affect histamine release during the early reaction to antigen.

Eight of the sixteen patients receive four prechallenge nasal lavages with IL-1 receptor diluted in buffer; the remaining ten receive lavages with buffer only. Thereafter, challenges with 1000 PNU of antigen are undertaken.

The patients maintain a symptom score sheet during the challenge procedure. In addition to the number of sneezes, a six-point scale from 0 to 5 (with 0 equal to no symptoms and 5 equal to severe symptoms) is used to assess nasal secretion, blockage, and itching. The degree of blockage is, of course, underestimated on those score sheets because of the pretreatment with oxymetazoline hydrochloride. The presence or absence of symptoms correlates with the presence or absence of mediators during the late reaction.

From a comparison of those patients receiving prechallenge treatment with IL-1 receptor and those receiving only buffer, it is clear that pretreatment with IL-1 receptor inhibits both the symptoms and the release of histamine and other inflammatory mediators during not only the late and rechallenge reactions to nasal challenge with antigen but also the early response.

Example 4

This example describes the use of soluble IL-1 receptor to reduce the late phase reaction (LPR) in lung tissue following inhalation of allergen.

Airway hyperactivity can be induced or worsened by antigen inhalation, exposure to some irritating chemicals, and by respiratory tract infections. The degree of reactivity is directly correlated with the number of mast cells and eosinophils detected by lavage.

In this example, twenty patients with documented allergic bronchial asthma participate. Allergen inhalation is performed by inhaling dust mite extract (see Example 1, above) at 15 minute intervals using a Wiesbadnener Doppelspray (8 L/min air flow, nebulizer output approximately 0.2 ml/min). Ten patients received the allergen premixed with IL-1 receptor; the other ten patients received the allergen alone.

Bronchoalveolar lavage performed 6 to 48 hours after inhalation of allergen alone shows increased numbers of eosinophils, mast cells, and desquamated epithelial cells. Eosinophil granule major basic protein levels are markedly elevated in the lavage fluid of these asthmatic patients. Peripheral blood eosinophil counts decrease during late phase responses to antigen challenge at the time eosinophil levels in the pulmonary tissues increases, presumably because of margination and emigration in the lungs.

Bronchoalveolar lavage after inhalation of allergen with IL-1 receptor shows suppression of eosinophil emigration in the lungs. The histologic data is consistent with the concept that activation of mast cells, infiltration of the tissues by eosinophils and other inflammatory cells, and tissue damage as well as dysfunction induced by inhalation of allergen is markedly suppressed by the presence of IL-1 receptor.

Thus it has been shown that the present invention provides beneficial methods and compositions for treating allergic reactions, including, without limitation, bronchial asthma, rhinoconjunctivitis, conjunctivitis, dermatitis, urticaria, chronic bronchitis, allergic and non-allergic rhinitis and inflammatory lung disease.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the appended claims.

We claim:

1. A method for treating tissue subject to reactions characterized as having late phase inflammatory responses comprising contacting the inflamed tissue with a preparation comprising at least one member selected from the group consisting of IL-1 receptors, TNF receptors, and receptor analogues thereof which are capable of binding either IL-1 or TNF.

2. The method of claim 1 wherein the inflammatory reaction is selected from the group consisting of cutaneous, ocular, nasal, gastrointestinal and bronchial reactions.

3. The method of claim 2 wherein the inflammatory reaction is selected from the group consisting of contact dermatitis, atopic dermatitis, urticaria, conjunctivitis, rhinitis, rhinoconjunctivitis, systemic anaphylaxis, asthma, hay fever, chronic bronchitis and inflammatory lung disease.

4. The method of claim 1 wherein a substantial proportion of the receptors or analogues contained in the preparation are soluble.

5. The method of claim 1 wherein the preparation comprises a mixture of IL-1 receptors and TNF receptors.

6. The method of claim 5 wherein at least a portion of said TNF receptors are covalently bound to said IL-1 receptors.

7. The method of claim 1 wherein the preparation comprises analogues of either IL-1 receptors or TNF receptors.

8. The method of claim 7 wherein at least a portion of said receptor analogues are hybrid fusion molecules comprising a TNF receptor moiety and an IL-1 receptor moiety.

9. The method of claim 1 wherein the preparation further comprises a therapeutically effective amount of at least one corticosteroid.

10. The method of claim 9 wherein at least a portion of said corticosteroids are covalently bound to said receptors.

* * * * *